United States Patent
Haggard et al.

(10) Patent No.: US 7,923,021 B2
(45) Date of Patent: Apr. 12, 2011

(54) LOCAL DELIVERY METHOD AND COMPOSITION

(75) Inventors: Warren O. Haggard, Bartlett, TN (US); Kelly C. Richelsoph, Belmont, NC (US)

(73) Assignee: University of Memphis Research Foundation, Memphis, TN (US)

( * ) Notice: Subject to any disclaimer, the term of this patent is extended or adjusted under 35 U.S.C. 154(b) by 252 days.

(21) Appl. No.: 12/178,312

(22) Filed: Jul. 23, 2008

(65) Prior Publication Data

US 2009/0028922 A1    Jan. 29, 2009

Related U.S. Application Data

(60) Provisional application No. 60/961,825, filed on Jul. 24, 2007.

(51) Int. Cl.
*A61F 2/00* (2006.01)

(52) U.S. Cl. ........................................ 424/423; 424/468

(58) Field of Classification Search .................. None
See application file for complete search history.

(56) References Cited

U.S. PATENT DOCUMENTS

| | | | |
|---|---|---|---|
| 6,391,336 B1 * | 5/2002 | Royer | 424/468 |
| 6,652,887 B1 * | 11/2003 | Richelsoph et al. | 424/549 |
| 6,913,764 B2 * | 7/2005 | Vogt et al. | 424/423 |
| 2004/0151753 A1 | 8/2004 | Chen | |
| 2005/0192236 A1 | 9/2005 | Chao | |
| 2006/0233851 A1 * | 10/2006 | Simon et al. | 424/422 |
| 2007/0086973 A1 | 4/2007 | Chowdhary | |
| 2007/0110804 A1 * | 5/2007 | Royer | 424/468 |

* cited by examiner

*Primary Examiner* — Robert A Wax
*Assistant Examiner* — Bethany Barham
(74) *Attorney, Agent, or Firm* — Harris, Shelton, Hanover & Walsh; Susan B. Fentress

(57) ABSTRACT

This invention provides a rapidly degrading composition for local delivery of a medicament, such as, an antibiotic. Additionally, this invention provides a method that can be used on the battlefield to deliver antibiotics as a preliminary treatment through the use of a rapidly degrading composition.

24 Claims, 4 Drawing Sheets

LOCAL DELIVERY METHOD AND COMPOSITION

CROSS-REFERENCE TO RELATED APPLICATION

This application claims the benefit of U.S. Provisional patent application Ser. No. 60/961,825 filed Jul. 24, 2007 under 35 USC §119(e) (hereby specifically incorporated by reference).

STATEMENT REGARDING FEDERALLY SPONSORED RESEARCH OR DEVELOPMENT

United States Army ISR Contract W8 1XWH-07-0206. The United States Army may retain certain rights.

REFERENCE TO SEQUENCE LISTING, A TABLE OR A COMPUTER PROGRAM LISTING, COMPACT DISC APPENDIX:

None.

BACKGROUND OF THE INVENTION

The present invention relates to a composition and a method to use the composition to rapidly deliver medicaments. During the management of modern battlefield musculoskeletal injuries, a need arose whereby soldiers could use an antibiotic-containing product, which could be easily applied in the field and would, in under 24 hours, release the contained antibiotic and completely dissolve. These fast resorbing and eluting attributes were needed as a preliminary treatment for wounded soldiers to prevent the establishment of serious infections.

BRIEF SUMMARY OF THE INVENTION

The present invention relates to a composition and method for rapid delivery of medicaments. The local delivery composition is made of calcium sulfate dihydrate and a binding agent formulated to dissolve within 24 hours of implantation. The composition also includes a medicament that is released, as the calcium sulfate dihydrate and the binding agent degrade. In the preferred embodiment, the binding agent is carboxymethylcellulose. Additionally, this invention provides a method to make local delivery composition involving the steps of: mixing calcium sulfate dihydrate, carboxymethylcellulose and a medicament in a solution to form a paste and evaporating the paste to form pellets.

This invention also provides a method to release medicament within twenty-four hours of implantation into a release environment by placing the local delivery composition of this invention into a release environment.

DETAILED DESCRIPTION OF THE INVENTION

Figure 1:
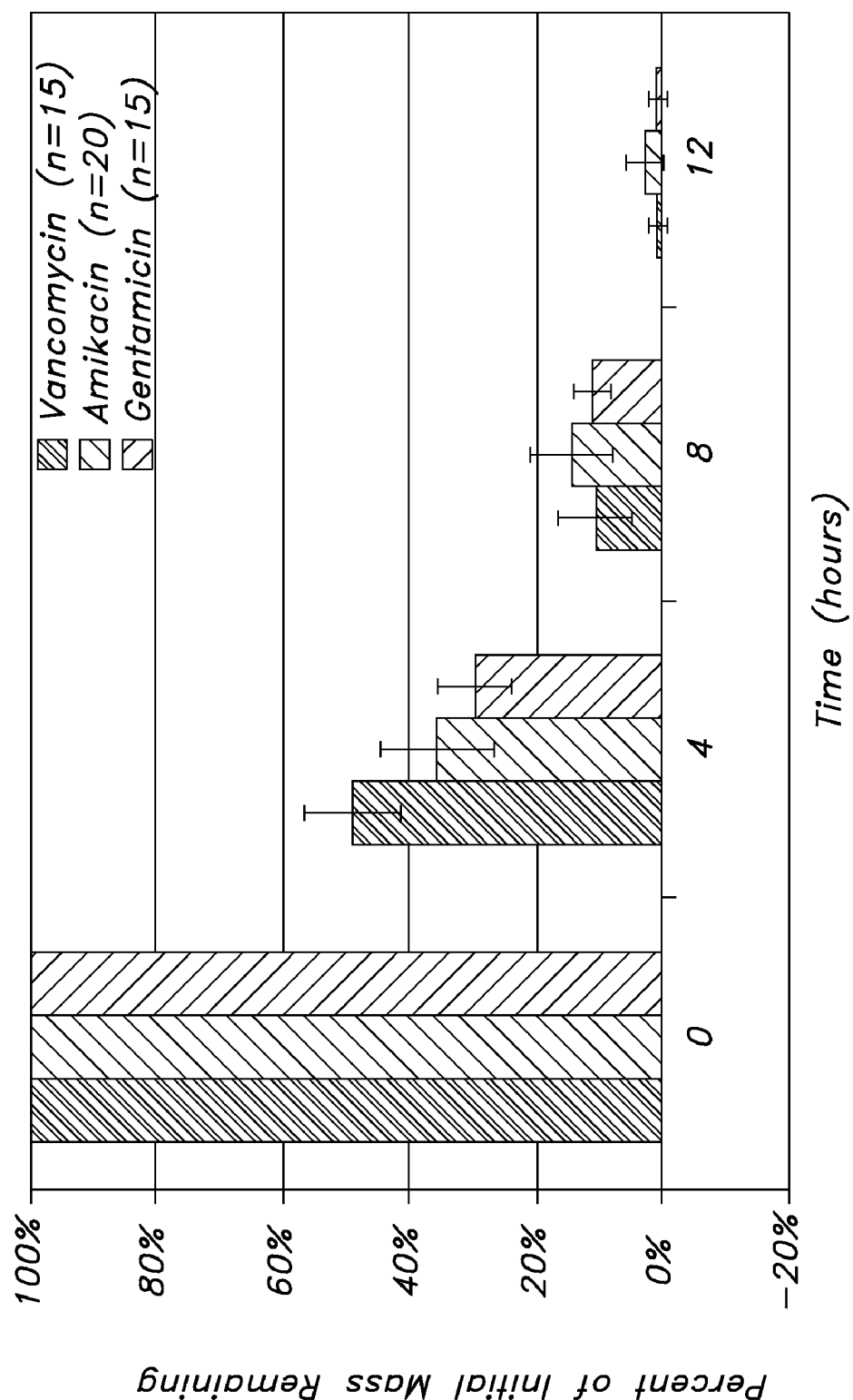
FIG. 1. shows dissolution of antibiotic-loaded calcium sulfate pellets. Dissolution of sterile calcium sulfate pellets loaded with 4% Amikacin™, Gentamicin™, or Vancomycin™.

The modification of calcium sulfate to accelerate both the dissolution rate of the pellet and elution rate of a contained medicament is the subject of this invention. Instead of using the conversion of hemihydrate to a dihydrate to produce a pellet, pellets were fabricated directly from calcium sulfate dihydrate. The calcium sulfate dihydrate was used as a biocompatible additive, an excipient, for pellet formation. A binder, such as the cellulose-based polymer, carboxymethylcellulose (CMC), was combined with the calcium sulfate dihydrate particles. The binding agent is provided to help obtain an implantable composition from the excipient and antibiotic paste. Examples of binding materials include sodium carboxymethylcellulose, methylcellulose, hydroxypropylmethylcellulose, hydroxypropylcellulose, ethylcellulose, hydroxyethycellulose and cellulose acetate butyrate. The binding agent is mixed with the calcium sulfate dihydrate in a mixing solution. Examples of mixing solutions include sterile water, saline, phosphate buffered saline, potassium chloride, sodium sulfate, potassium sulfate, EDTA, ammonium sulfate, ammonium acetate and sodium acetate.

When hydrated, the carboxymethylcellulose swells and thickens the mixture. After drying, the carboxymethylcellulose effectively holds the pellets together, however, they are prone to a rapid dissolution and resulting elution of a contained medicament upon exposure to a moist environment. These calcium sulfate pellets bound with carboxymethylcellulose have the rapid dissolution and degradation profiles for rapid delivery of medicaments. Multiple antibiotics, or other medicaments, such as anesthetics and growth factors call be incorporated within the pellet. The term "medicament", as used in the application means antibiotics, anesthetics, growth factors and/or other therapeutic agents.

To increase the dissolution rate and elution rate of medicament-loaded calcium sulfate, a matrix formed from calcium sulfate dihydrate, carboxymethylcellulose, medicament, and water was mixed together and molded into the form of a pellet. When mixed, the carboxymethylcellulose dissolved and swelled in solution and formed a calcium sulfate dihydrate paste, which was easily molded. Upon air-drying, the water was evaporated, but the matrix was mechanically interlocked by the carboxymethylcellulose, with the medicament loosely attached to the surface of the dihydrate and carboxymethylcellulose particles. When dried pellets were placed into a release environment, such as, phosphate buffered saline at 37° C., or the like, the medicament content was completely released as the pellets disintegrated in less than 24 hours. A release environment is preferably a complex musculoskeletal injury, open wound or burn of a patient.

Multiple antibiotics, or other medicaments, such as anesthetics and growth factors call be incorporated with the fast resorbing calcium sulfate. The term "medicament", as used in the application means antibiotics, anesthetics, growth factors and/or other therapeutic agents.

Calcium sulfate pellets containing Amikacin™ were by combining with 5 g of calcium sulfate dihydrate, 0.2 g of carboxymethylcellulose, 0.210 g of Amlikacin™, and 4.2 ml of deionized (DI) water. Our preferred ratio is 10 g of $CaSO_4$ to 0.4 g of antibiotics to 0.4 g of CMC. The antibiotic level in the pellet can range from the experimental level of approximately 4% to about 12% if needed. The ingredients were mixed thoroughly until a paste formed. The paste was then cast into a silicone pellet mat: producing cylindrical pellets 3.0 mm diameter and 4.8 mm height. The pellets were allowed to dry completely at room temperature. It should be recognized that with different molds, other shapes (such as spheres) can be manufactured using the same methodology.

Antibiotic-loaded pellets were made by mixing 10.0 g pharmaceutical grade calcium sulfate dihydrate powder with 0.40 g sodium carboxymethylcellulose. A solution was prepared by mixing antibiotic (0.42 g Amikacin Sulfate™ or Gentamicin Sulfate™ or 0.43 g Vancomycin™ (Hydrochloride) with 8.4 g deionized water. The antibiotic solution was poured over the Terra Alba and CMC powders, and then the materials were mixed briskly for 1 minute. The resulting 4% antibiotic-loaded paste was cast into silicone elastomer molds and allowed to dry for 24 hours at room temperature. Once dry, the cylindrically shaped pellets (4.7 mm height, 3.4 mm diameter, 40±2 mg weight) were demolded and sterilized using low-dose gamma irradiation (25 kGy).

Conventional calcium sulfate alpha-hemihydrate Gentamicin™ pellets were cast by mixing 1.04 g Gentamicin™ sulfate powder with 5.0 g deionized water. The antibiotic solution was poured over 20.0 g calcium sulfate alpha-hemihydrate and mixed briskly for 1 minute. M. McKee, *The Use of an Antibiotic Impregnated, Osteoconductive, Bioabsorbable Bone Substitute in the Treatment of Infected Long Bone Defects: Early Results of a Prospective Trial.* 16 Orthopedic Trauma 1218-1244 (2002). The resulting 4% antibiotic-loaded paste was cast into silicone elastomer molds and left to dry overnight at room temperature. After drying completely, the pellets were demolded and sterilized using low-dose gamma irradiation (25 kGy). Each pellet was 4.7 mm in height, 3.4 mm in diameter, and 105±4 mg in weight. The sterilized pellets were then crushed using a mortar and pestal into fine-and coarse-sized flakes. The flake diameter of finely ground flakes was 150 μm (range=0-300 μm), while that of coarsely ground flakes was 600 μm (range=0-1200 μm). Flake size was verified using an inverting light microscope and image processing software (Bioquant Osteo II, Bioquant Image Analysis, Nashville, Tenn.).

To evaluate dissolution of the pellets, individual pellets or the equivalent of one pellet in flakes (n≧3) were immersed in 100 ml of deionized water in a 37° C. water bath. At specified time intervals (t=1, 4, 8, 12, 24, 36, 48, 72, 96, 120, 144 hours), pellets were removed, oven dried at 37° C. for 1 hour and weighed. After weighing, the pellets were re-immersed in fresh DI water. Testing continued until pellets were completely dissolved. Testing was repeated for three batches of pellets.

Elution was characterized by placing groups of eight pellets or the flakes of eight pellets (n≧3) in 20 ml phosphate buffered saline (PBS) in a 37° C. water bath. At specified times (t=1, 4, 8, 12, 24, 36, 48, 72, 96, 120, 144, 168, 240 hours), aliquots were removed and frozen at −40° C. At each time interval, the pellets were removed and placed in 20 ml fresh PBS. The amount of antibiotic in the eluates was determined (μg/ml) using a Florescence Polarization Immunoassay (TDxFLx, Abbott Laboratories, Abbott Park, Ill.). Testing was repeated for three batches of pellets.

*Pseudomonas aeruginosa* strain ATCC 27317 was used for biological activity testing of Amikacin™ and Gentamicin™ eluates. A clinical isolate of *Staphylococcus aureus* Cowan I strain was used to assess activity of Vancomycin™ eluates. The eluate having the lowest concentration for each antibiotic at each of the specified time points was used in the biological activity assay. *P. aeruginosa* or *S. aureus* was grown overnight at 37° C. in Trypticase soy broth (TSB). Conical tubes were prepared with 1.75 ml of TSB and 200 μl of antibiotic dilutions (Amikacin™: 0-640 μg/ml, Gentamicin™: 0-2560 μg/ml, Vancomycin™: 0-160 μg/ml), or 200 μl eluate samples, or 200 μl buffer. All tubes except blanks were inoculated with 50 μl of 1:50 dilution of bacteria. Blanks were supplanted with an additional 50 μl of TSB instead of bacteria. The tubes were vortexed and incubated at 37° C. for 24 hours. A blank was used to adjust the spectrophotometer to zero, and the absorbance at 530 nm ($A_{530}$) was recorded. Results were reported as percent growth relative to control, calculated as ($A_{530}$ sample/$A_{530}$ control)×100. This method dilutes the sample concentration by a factor of 10. Testing was repeated for three replicates of the samples.

Statistical analyses included two-factor ANOVA and multiple comparisons tests with significance set at the alpha=0.05 level. For pellets, difference in the dissolution or elution rate based on the antibiotic incorporated was evaluated. Gentamicin™-loaded pellets were compared to conventional pellet flakes by analyzing differences in dissolution or elution rate based on treatment type (pellet, fine flakes, coarse flakes).

As shown in FIG. 1 sterile pellets dissolve completely between 12-16 hours. Significant differences were only observed in the dissolution rates of Gentamicin™-and Vancomycin™-loaded pellets (p<0.01), with Gentamicin™-loaded pellets dissolving more rapidly than Vancomycin™-loaded pellets. In general, for all antibiotics, 50% to 70% of the pellet was dissolved within four hours, 85-90% within 8 hours, more than 95% within 12 hours, and no pellet remained at hour 16.

Figure 2:
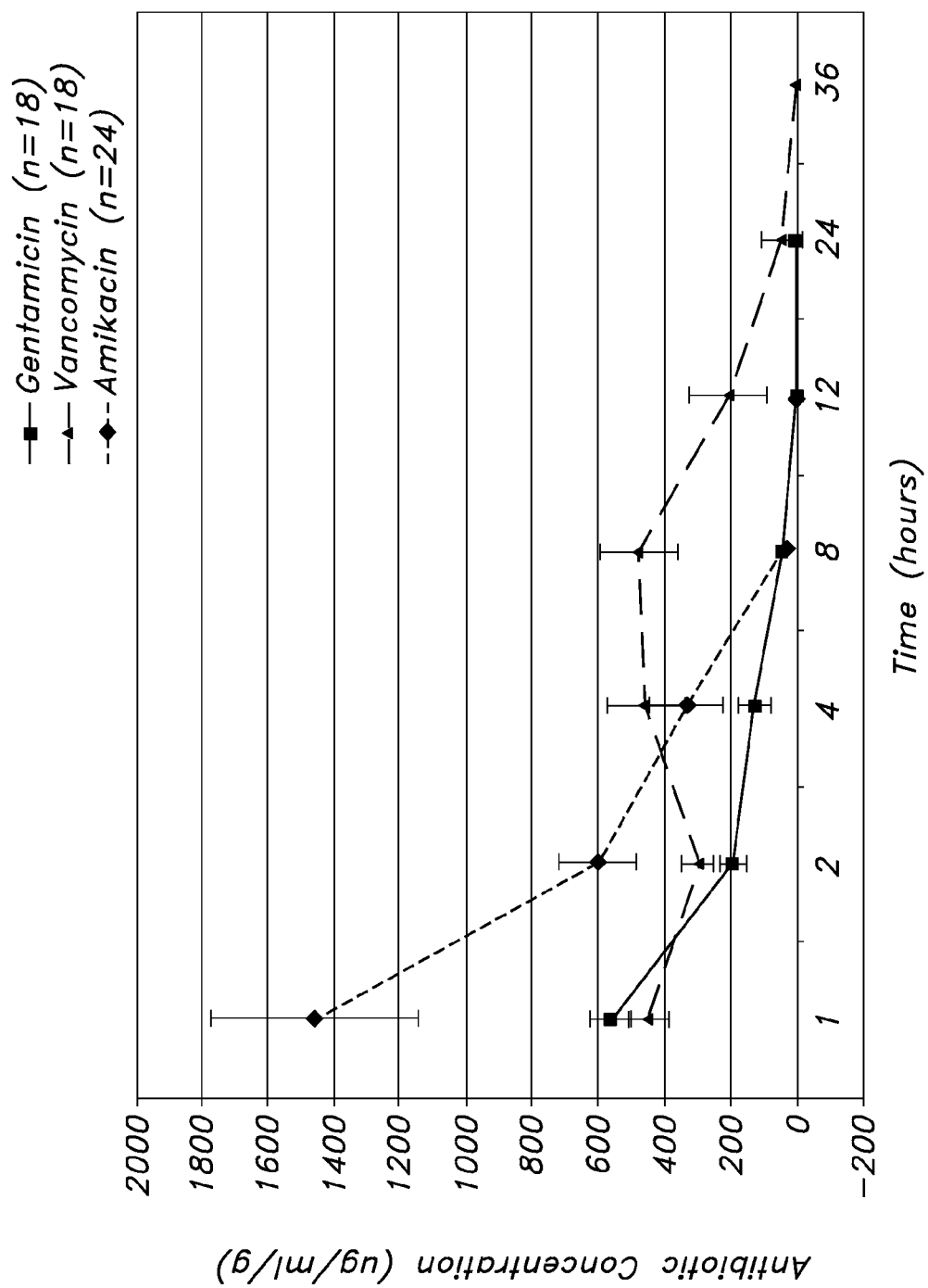
FIG. 2. shows elution of antibiotic-loaded calcium sulfate pellets. Elution of antibiotics from sterile calcium sulfate pellets loaded with 4% Amikacin™, Gentamicin™, or Vancomycin™.

FIG. 2. illustrates Amikacin™, Gentamicin™, and Vancomycin™ elution from pellets. There are differences in the elution rate for Vancomycin™/Amikacin™ (p=0.04), but not Amikacin™/Gentamicin™ and Vancomycin™/Amikacin™. Qualitatively, the elution profiles for Gentamicin™ and Amikacin™ both peak at hour one and decrease exponentially over the life of the pellets. The Vancomycin™ elution profile shows a burst of antibiotic in hour one, followed by a smaller release at hour two, another burst for hours four and eight, and a relatively stable decrease for the remaining life of the pellet. Substantially, all of the antibiotics is released within twenty-four hours as the pellet dissolves.

Figure 3:
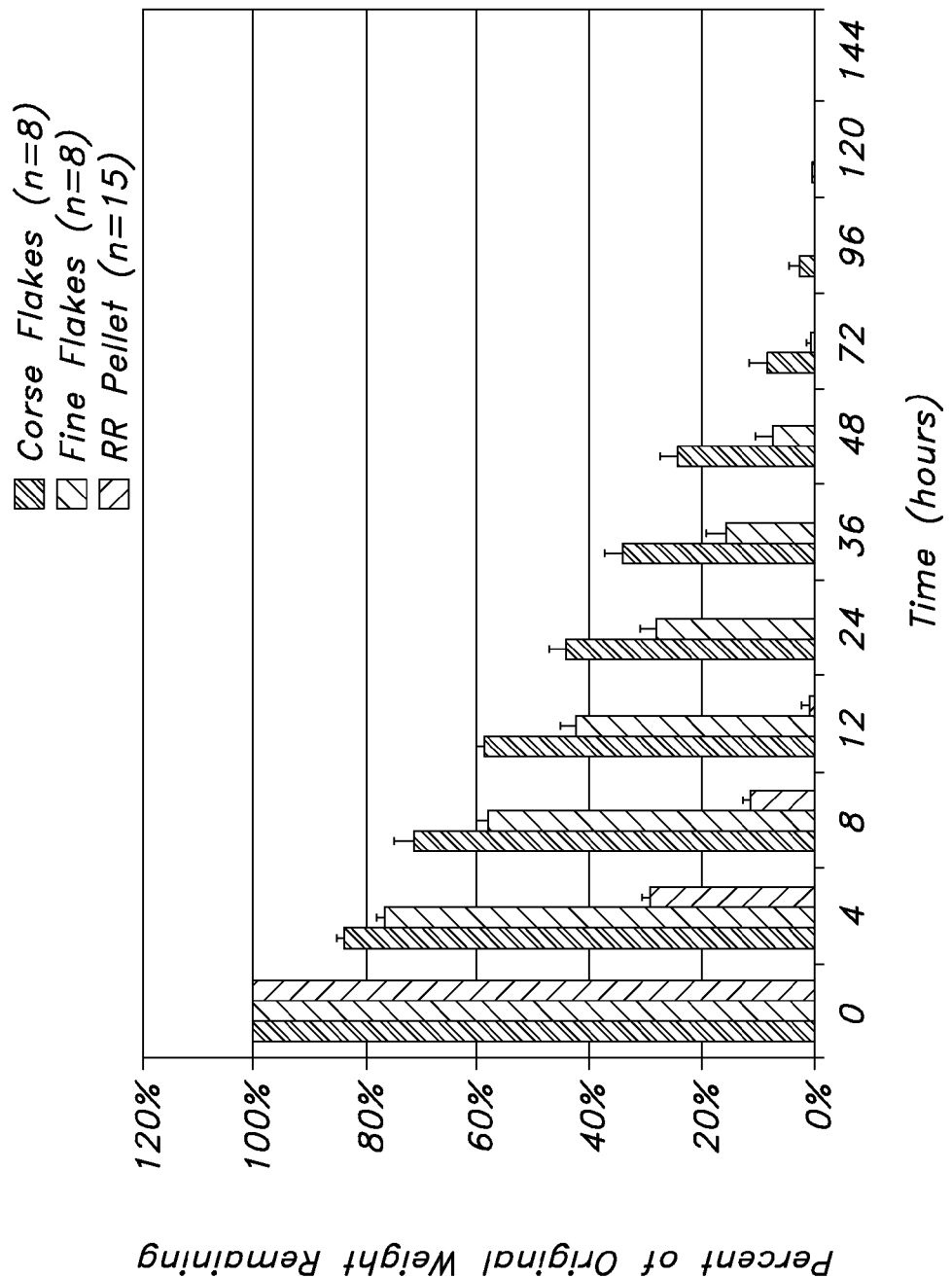
FIG. 3. shows dissolution profile comparison for Gentamicin™-loaded rapidly resorbing pellets and conventional pellet flakes. Dissolution profiles for Gentamicin™-loaded pellets and Gentamicin™-loaded conventional calcium sulfate pellet flakes crushed into fine or coarse size.

FIG. 3 plots dissolution rates for Gentamicin™-loaded pellet, coarse flake, and fine flake, which differ from one another (p<0.001). The dissolution rates are significantly different for fine and coarse conventional calcium sulfate pellet flakes (p<0.001). Coarse-and fine-sized conventional Gentamicin™-loaded calcium sulfate pellet flakes dissolve in 4-6 days. Over 50% of the flake mass has dissolved in 12 hours for fine flakes and in 24 hours for coarse flakes.

Figure 4:
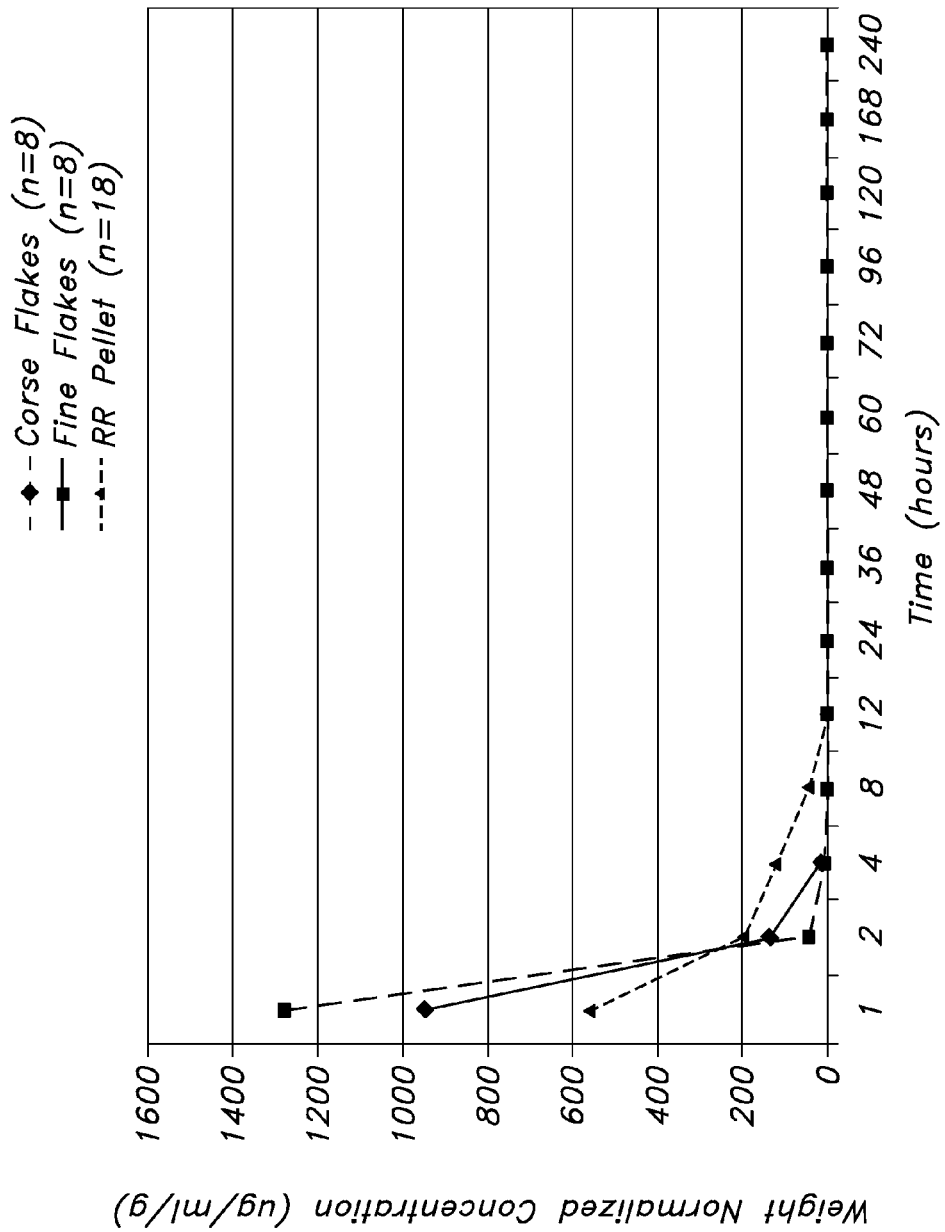
FIG. 4. shows elution profile comparison for Gentamicin™-loaded rapidly resorbing pellets and conventional pellet flakes. Elution profiles for Gentamicin™-loaded pellets and Gentamicin™-loaded conventional calcium sulfate pellet flakes crushed to fine or coarse size.

FIG. 4 graphs the elution profiles for coarse flake, fine flake, and pellet formulations with Gentamicin™. The elution rate for coarse and fine pellet flakes differs only over the first four hours (p<0.001). Similar elution profiles were found for coarse flakes and Gentamicin™ pellets for the first 24 hours (p=0.740). Elution beyond 24 hours was not compared since the fast resorbing pellet sample had completely dissolved by this time point.

Biological activity results are provided in Table 1. The observed minimum inhibitory concentration (MIC) of *P.*

*aeruginosa* ATCC 27317 treated with Amikacin™ or Gentamicin™ was 4.0 ug/ml, which is within the range of the published literature. A Endimiani et al. *Pseudomonas aeruginosa Bloodstream Infections: Risk Factors and Treatment Outcome Related to Expression of the PER-1 Extended-Spectrum Beta-Lacatamase*, 6 BMC Infect Dis 52 (2006). Both Gentamicin™-and Amikacin™-loaded pellet eluates completely inhibit growth of *P. aeruginosa* for hours 1, 2, and 4, as they maintain antibiotic concentration above the MIC. The MIC for *S. aureus* Cowan I clinical isolate with Vancomycin™ was determined to be 0.5 µg/ml. R S Schwalbe, et a.l *Emergence of Resistance In Coagulase Negative Staphylococci*. 361 New England Journal of Medicine 927-931 (1987). Vancomycin™-loaded pellets were active against *S. aureus* through hour 12. At hour 24, the Vancomycin™ concentration falls below the MIC. For both coarse-and fine-flake experiments, only the first hour sample contained sufficient antibiotic to effectively inhibit growth of *P. aeruginosa*.

TABLE 1

| | Organism | | | | |
|---|---|---|---|---|---|
| | S. aureus | P. aeruginosa ATCC 27317 | | | |
| Timepoint (hours) | Cowan I RR + Vanc ™ | RR + Amik ™ | RR + Gent ™ | CF + Gent ™ | FF + Gent ™ |
| 1 | − | − | − | − | − |
| 2 | − | − | − | + | + |
| 4 | − | − | − | + | + |
| 8 | − | + | + | + | + |
| 12 | − | + | + | + | + |
| 24 | + | + | + | + | + |
| 48 | + | + | + | + | + |
| 240 | / | / | / | + | + |

Table 1. Growth of *P. aeruginosa* or *S. aureus* in the presence of rapidly resorbing pellet eluates or conventional pellet flake eluates diluted by a factor of 10. (−) indicates no growth, (+) indicates growth. RR, rapidly resorbing calcium sulfate pellet; Vanc, Vancomycin™; Amik, Amikacin™; Gent, Gentamicin™; CF, coarse conventional calcium sulfate pellet flakes; FF, fine conventional calcium sulfate pellet flakes.

A number of embodiments of the invention have been described. Nevertheless, it will be understood that various modifications may be without departing from the spirit and scope of the invention.

We claim:

1. A local delivery composition comprising:
a paste comprising calcium sulfate dihydrate, a medicament, a mixing solution and a binding agent, wherein said paste is treated to form a pellet, said pellet formulated to dissolve within 24 hours of implantation in a release environment wherein said release environment is selected from the group consisting of an open wound, tissue of a burn patient and a musculoskeletal injury.

2. A local delivery composition comprising:
a paste comprising calcium sulfate dihydrate, a medicament, a mixing solution and carboxymethylcellulose, wherein said paste is treated to form a pellet and said medicament is retained in said pellet wherein said pellet substantially dissolves in a release environment within 24 hours of implantation in said release environment.

3. A method to make a local delivery composition comprising:
a) mixing calcium sulfate dihydrate, a binding agent and a medicament in a mixing solution to form a paste; and
b) evaporating said solution to form a pellet.

4. The method of claim 3 wherein said pellet is sterilized by gamma radiation.

5. A method to release a medicament within twenty-four hours of implantation comprising placing the composition of claim 1 into a release environment and releasing said medicament to the environment within twenty-four hours.

6. A method to release a medicament within twenty-four hours of implantation comprising placing the composition of claim 2 into a release environment and releasing said medicament to the environment within twenty-four hours.

7. The composition of claim 1 wherein said calcium sulfate dihydrate comprises 92.6%, said medicament 3.7% and said binding agent 3.7% of said local delivery composition.

8. The composition of claim 7 wherein said binding agent is carboxymethylcellulose.

9. The composition of claim 1 wherein said medicament is an antibiotic and said antibiotic comprises about 4 percent by weight of said local delivery composition.

10. The composition of claim 2 wherein said medicament is an antibiotic and said antibiotic comprises about 4 percent by weight of said local delivery composition.

11. A local delivery composition comprising:
a calcium sulfate dihydrate and a binder formulated to dissolve within 24 hours of implantation in a release environment and a medicament wherein said local delivery agent is in the form of a pellet, and made by the process comprising:
mixing calcium sulfate dihydrate, a binding agent and a medicament in a mixing solution to form a paste; and
evaporating said solution to form a pellet.

12. The composition of claim 11 wherein the binding agent is carboxymethylcellulose.

13. The composition of claim 12 wherein said calcium sulfate dihydrate comprises 92.6%, said medicament 3.7% and said carboxymethylcellulose 3.7% of said local delivery composition.

14. The method of claims 5 wherein the release environment is an open wound.

15. The method of claims 5 wherein the release environment is the tissue of a burn patient.

16. The method of claims 5 wherein the release environment is a musculoskeletal injury.

17. The method of claim 3 wherein the binding agent is carboxymethylcellulose.

18. The method of claim 3 wherein the mixing solution is selected form the group consisting of: sterile water, saline, phosphate buffered saline, potassium chloride, potassium sulfate, EDTA, ammonium sulfate, ammonium acetate and sodium acetate.

19. The method of claim 3 wherein the binding agent is select form the group consisting of methylcellulose, hydroxypropylmethylcellulose, hydroxypropylcellulose, ethylcellulose, hydroxyethycellulose and cellulose acetate butyrate.

20. The composition of claim 2 wherein in said release environment is selected from the group consisting of an open wound, tissue of a burn patient and a musculoskeletal injury.

21. The composition of claim 1 wherein said medicament is Vancomycin and the minimum inhibitory concentration is sustained for at least twelve hours from implantation in a release environment.

22. The composition of claim 2 wherein said medicament is Vancomycin and the minimum inhibitory concentration is sustained for at least twelve hours from implantation in a release environment.

23. The composition of claim 1 wherein said medicament is selected from the group consisting of Amikacin and Gentamicin and the minimum inhibitory concentration is sustained for at least four hours from implantation in a release environment.

24. The composition of claim 2 wherein said medicament is selected from the group consisting of Amikacin and Gentamicin and the minimum inhibitory concentration is sustained for at least four hours from implantation in a release environment.

* * * * *